United States Patent [19]
Real et al.

[11] Patent Number: 5,610,308
[45] Date of Patent: Mar. 11, 1997

[54] PROCESS FOR PREPARING INTERMEDIATES FOR THROMBIN INHIBITORS

[75] Inventors: Sharon D. Real, San Diego, Calif.; David R. Kronenthal, Yardley, Pa.

[73] Assignee: Bristol-Myers Squibb Company, Princeton, N.J.

[21] Appl. No.: 443,960

[22] Filed: May 18, 1995

[51] Int. Cl.⁶ .................................................. C07D 211/60
[52] U.S. Cl. .......................... 546/208; 540/454; 540/470; 540/480; 540/481; 540/544; 540/596; 540/597; 540/575; 540/602; 544/60; 544/129; 544/141; 544/365; 544/372; 546/189; 548/518
[58] Field of Search ..................... 540/454, 470, 540/480, 481, 544, 596, 597, 602, 575; 544/60, 129, 141, 365, 372; 546/189, 208; 548/518

[56] References Cited

U.S. PATENT DOCUMENTS 5,498,724  3/1996  Nyström et al. ................. 548/375.1

FOREIGN PATENT DOCUMENTS

0601459A2  6/1994  European Pat. Off. .
WO9429269  12/1994  WIPO .

OTHER PUBLICATIONS

Bernatowicz, M. S. et al, "Urethane Protected Derivatives of 1–Guanylpyrazole for the Mild and Efficient Preparation of Guanidines", Tetrahedron Letters, vol. 34, No. 21, pp. 3389–3392 (1993).

*Primary Examiner*—C. Warren Ivy
*Assistant Examiner*—Garth M. Dahlen
*Attorney, Agent, or Firm*—Burton Rodney

[57] ABSTRACT

A process is provided for preparing intermediates of the structure

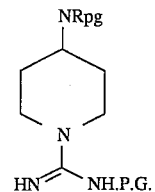

wherein Rpg is preferably $=CHC_6H_5$; and P.G. is a protecting group CBZ or BOC, wherein a protected guanylpyrazole is reacted with an azacycloalkyl, azacycloalkenyl or azaheteroalkyl derivative (such as a piperidine derivative) in the presence of a DBU catalyst. The resulting intermediate may be used as a starting material for preparing thrombin inhibitors.

16 Claims, No Drawings

PROCESS FOR PREPARING INTERMEDIATES FOR THROMBIN INHIBITORS

FIELD OF THE INVENTION

The present invention relates to a process for preparing a substituted guanidine intermediate which is useful for preparing thrombin inhibitors.

BACKGROUND OF THE INVENTION

U.S. application Ser. No. 146,714 filed Nov. 10, 1993 ((file HA619b) (incorporated herein by reference) now abandoned, discloses thrombin inhibitors of the structure

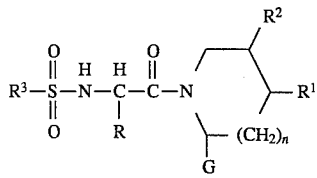

including all stereoisomers, wherein n is 0, 1 or 2;

G is an amido moiety which includes a cyclic member;

R is hydrogen, hydroxyalkyl, aminoalkyl, alkyl, cycloalkyl, arylalkyl, alkenyl, alkynyl, amidoalkyl, arylalkoxyalkyl or an amino acid side chain, either protected or unprotected;

$R^1$ and $R^2$ are independently hydrogen, lower alkyl, cycloalkyl, aryl, hydroxy, alkoxy, keto, thioketal, thioalkyl, thioaryl, amino or alkylamino; or $R^1$ and $R^2$ together with the carbons to which they are attached form a cycloalkyl, aryl or heteroaryl ring;

$R^3$ is alkyl, arylalkyl, aryl, heteroaryl, quinolinyl or tetrahydroquinolinyl;

including pharmaceutically acceptable salts thereof, and G is

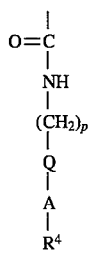

wherein p is 0, 1 or 2;

Q is a single bond or

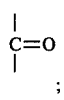

;

A is aryl or cycloalkyl or an azacycloalkyl ring of 4 to 8 members or an azaheterocycloalkyl ring of 6 to 8 members of the structure

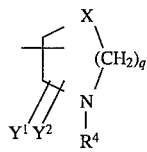

where X is $CH_2$, O, S or NH;

q is 0, 1, 2, 3 or 4, provided that q is 0, 1, 2, 3 or 4 if X is $CH_2$;

q is 2, 3 or 4 if X is O, S or NH;

$y^1$ and $y^2$ are independently H, lower alkyl, halo or keto;

$R^4$ is guanidino, amidino or aminomethyl; with the provisos that where A is aryl or cycloalkyl, $R^4$ is guanidino, amidino or aminomethyl, where A is azacycloalkyl or azaheterocycloalkyl, $R^4$ is amidino;

where A is azaheterocycloalkyl, then there must be at least a 2-carbon chain between X and any N atom in the ring or outside the ring.

DESCRIPTION OF THE INVENTION

In accordance with the present invention, a process is provided for preparing a guanidine intermediate of the structure

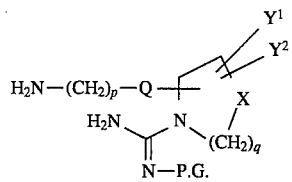

wherein p is 0, 1 or 2;

Q is a single bond or

;

$Y^1$ and $Y^2$ are independently H, lower alkyl or halo;

X is $CH_2$, —CH=CH—, O, S or NH;

q is 0, 1, 2, 3 or 4 if X is $CH_2$ or —CH=CH—;

q is 2, 3 or 4 if X is O, S or NH;

and P.G. is an amine protecting group which preferably is benzyloxycarbonyl (CBZ) or t-butoxycarbonyl (BOC), and the N-, X-containing ring is referred to as azacycloalkyl, azacycloalkenyl, azaheterocycloalkyl or the A ring, which process includes the steps of providing a protected guanylpyrazole of the structure

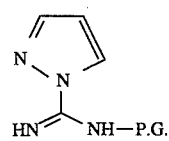

where P.G. is as defined above, and reacting the protected guanylpyrazole II with a compound of the structure

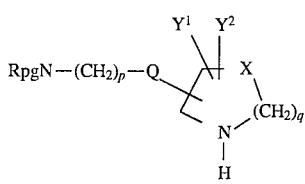

III where p, Q, x, q and $Y^1$ and $Y^2$ are as defined above and Rpg is an N-protecting group, for example, a Schiff base such as $=CHC_6H_5$, CBZ, or BOC in the presence of a basic catalyst, such as triethyl-amine, or diisopropylethylamine, and preferably 1,8-diazabicyclo-[5.4.0]undec-7-ene (DBU) or 1,5-diazabicyclo-[4.3.0]non-5-ene (DBN), to form the guanidine intermediate I.

Starting material III may be prepared by reacting the corresponding unprotected amino compound IIIA

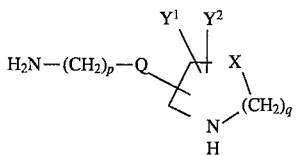

IIIA with an aldehyde such as benzaldehyde at a temperature within the range from about 25° C. to about 120° C.

In addition, in accordance with the present invention, a process is provided for employing the substituted piperidinoguanidine intermediate I for preparing sulfonamido heterocyclic thrombin inhibitors of the structure

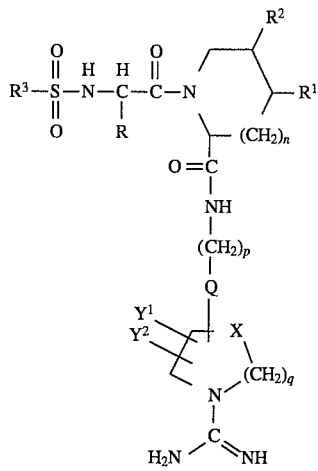

IV

R is hydrogen, hydroxyalkyl, aminoalkyl, amidoalkyl, alkyl, cycloalkyl, aryl, arylalkyl, alkenyl, alkynyl, arylalkoxyalkyl, or an amino acid side chain, either protected or unprotected;

$R^1$ and $R^2$ are independently hydrogen, lower alkyl, cycloalkyl, aryl, hydroxy, alkoxy, oxo (also referred to as keto), thioxo, thioketal, thioalkyl, thioaryl, amino or alkylamino; or $R^1$ and $R^2$ together with the carbons to which they are attached form a cycloalkyl, aryl, or heteroaryl ring; and $R^3$ is lower alkyl, aryl, arylalkyl, heteroaryl, quinolinyl or tetrahydroquinolinyl;

n is 0, 1 or 2;

and p, Q, X, q, $Y^1$ and $Y^2$ are as defined hereinbefore.;

provided that where x is a hetero atom (that is, A ring is azaheterocycloalkyl), then there must be at least a 2-carbon chain between x and any N atom in the ring outside the ring A;

which process includes the steps of providing the substituted piperidinoguanidine intermediate I, reacting the guanidine intermediate I with an acid of the structure V

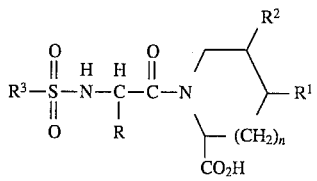

V in a carbodiimide coupling reaction, in the presence of a coupling agent such as ethyl 3-(3-dimethylamino-)propyl carbodiimide hydrochloride (WSC) or dicyclohexyl-carbodiimide (DCC) or diisopropyl-carbodiimide (DIC), and 1-hydroxybenzotriazole monohydrate (HOBT), and optionally in the presence of a suitable base such as N-methylmorpholine (NMM) or triethylamine, and in the presence of a solvent such as aqueous isopropanol, dimethylformamide (DMF), THF, dichloromethane, or N-methylpyrrolidone, to form the protected compound VI

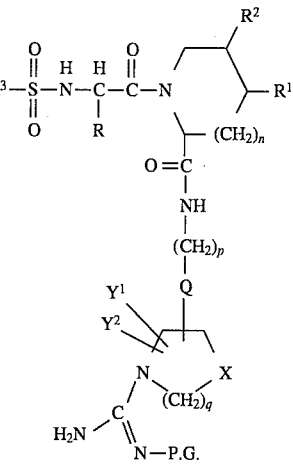

VI and removing the protecting group, by standard deprotection procedures, for example, by hydrogenation where P.G. is CBZ, or by treatment with trifluoroacetic acid or anhydrous HCl where P.G. is BOC, to form the guanidine thrombin inhibitor Iv.

Thus, through use of the substituted piperidinoguanidine intermediates I, prepared in accordance with the process of the invention, thrombin inhibitors IV as essentially disclosed in U.S. application Ser. No. 146,714 mentioned above may be prepared.

In accordance with the present invention, a preferred process is provided for preparing an intermediate of the structure

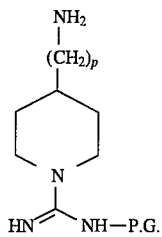

IA wherein P.G. is an amine protecting group such as benzyloxycarbonyl (CBZ) or t-butoxycarbonyl (BOC), which process includes the steps of providing a protected guanylpyrazole of the structure II

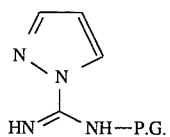

II where P.G. is a protecting group as defined above, and reacting the protected guanylpyrazole II with a piperidine derivative of the structure IIIB

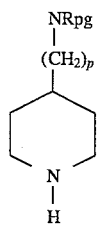

IIIB where Rpg is a protecting group such as CBZ, BOC or a Schiff base derivative, preferably $=CHC_6H_5$. However, it will be understood that the protecting group Rpg will always differ from the protecting group P.G. The reaction is carried out in the presence of a basic catalyst as defined above, and in an inert organic solvent such as DMF, or preferably acetonitrile. Thereafter, the protecting group Rpg is removed by conventional techniques to form the substituted piperidinoguanidine intermediate I.

In another aspect of the present invention, a preferred process is provided for employing the substituted piperidinoguanidine intermediate I to prepare a thrombin inhibitor IV. In the preferred embodiment of the invention, the substituted piperidinoguanidine intermediate IA is coupled with an acid compound of the structure VA

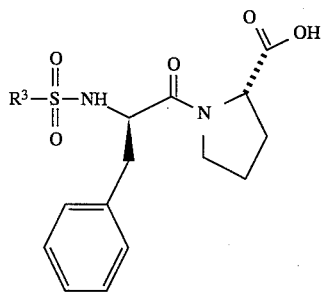

VA wherein $R^3$ is preferably alkyl, aryl, or arylalkyl, more preferably methyl or benzyl, in a carbodiimide coupling reaction, as described hereinbefore, to form protected guanidine thrombin inhibitor of the structure VIA

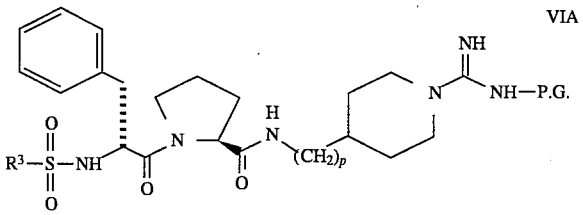

VIA where $R^3$ is preferably $CH_3$ or benzyl.

Guanidine thrombin inhibitor VIA is deprotected, for example, where P.G. is CBZ, by hydrogenation to form guanidine thrombin ihnibitor IVA

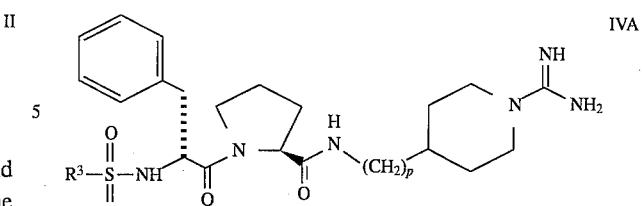

IVA where $R^3$ is preferably $CH_3$ or benzyl.

The guanidine thrombin inhibitor VIA may be reacted with an organic acid, such as acetic acid or with a hydrohalic acid, such as HCl to form a pharmaceutically acceptable salt as described in detail hereinafter.

DETAILED DESCRIPTION OF THE INVENTION

In carrying out the process of the invention, in forming intermediate I (or IA), the protected guanylpyrazole II will be employed in a molar ratio to III (or IIIB) within the range from about 1:1 to about 3:1, preferably from about 1.1:1 to about 2:1. The reaction of II and III (or IIIB) will be carried out at a temperature within the range from about 20° C. to about 70° C., preferably from about 40° C. to about 60° C., preferably under an inert atmosphere such as nitrogen or argon.

The basic catalyst employed in the reaction of II and III (or IIIB) will include DBU, DBN, triethylamine or diisopropylethylamine, preferably DBU or DBN, and will be employed in a molar ratio to III within the range from about 1:1 to about 3:1, preferably from about 1.1:1 to about 2:1.

In carrying out the process of the invention for forming thrombin inhibitor IV (or IVA), intermediate I (or IA) will be employed in a molar ratio to V (or VA) within the range from about 1.1:1 to about 3:1, preferably from about 1.1:1 to about 2:1, and the coupling reaction will be carried out at a temperature within the range from about 0° C. to about 30° C., preferably from about 5° C. to about 20° C.

The starting material V may be prepared as set out in the following reaction sequence.

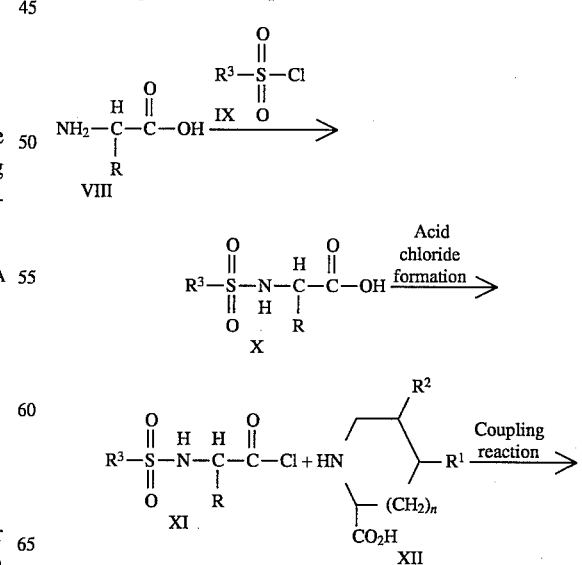

-continued

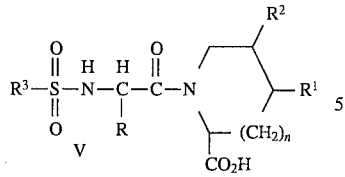

As seen in the above reaction sequence, compounds of formula V are prepared as follows.

Amino acid VIII is reacted with sulfonyl chloride IX in the presence of aqueous base such as NaOH, and optionally in the presence of an organic cosolvent, to form sulfonamide X. Sulfonamide x is subjected to acid chloride formation by treating x with oxalyl chloride or thionyl chloride in the presence of an inert organic solvent and catalytic amounts of DMF to form acid chloride XI. Acid chloride XI is coupled with acid XII in the presence of aqueous base, and optionally in the presence of an organic cosolvent, to form V.

Examples of the A ring (azacycloalkyl, azacycloalkenyl or azaheterocycloalkyl) which may be employed herein include

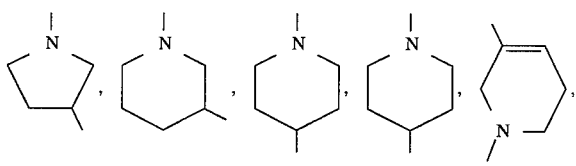

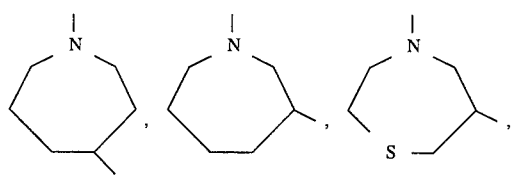

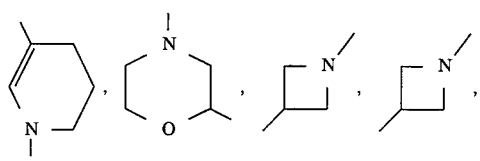

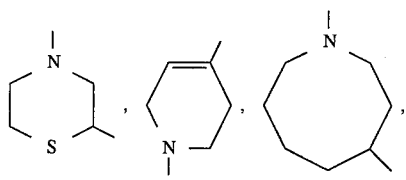

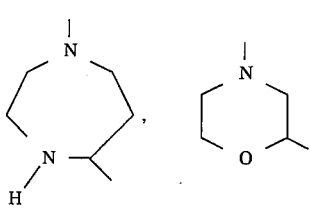

and the like.

Preferred are compounds wherein Q is a single bond and A is an azacycloalkyl ring

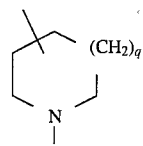

where q is 0 or 1; and
$R^3$ is lower alkyl or aryl;
R is aralkyl or hydroxyalkyl;
$R^1$ and $R^2$ are each H;
n is 0 or 1.

IN GENERAL

The term "lower alkyl" or "alkyl" as employed herein by itself or as part of another group includes both straight and branched chain radicals of up to 18 carbons, preferably 1 to 8 carbons, such as methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, the various branched chain isomers thereof, and the like as well as such groups including 1, 2 or 3 halo substituents (for example, to form $CF_3$ or $CF_3CH_2$) and/or 1 or 2 of the following substituents: an aryl substituent (for example, to form benzyl or phenethyl), an alkyl-aryl substituent, a haloaryl substituent, a cycloalkyl substituent, an alkylcycloalkyl substituent, an alkenyl substituent, an alkynyl substituent, hydroxy or a carboxy substituent. It will be appreciated that the same "alkyl" group may be substituted with one or more of any of the above substituents.

The term "cycloalkyl" by itself or as part of another group includes saturated cyclic hydrocarbon groups containing 3 to 12 carbons, preferably 3 to 8 carbons, which include cyclopropyl, cyclobutyl, cyclopentyl, cyclohexyl, cycloheptyl, cyclooctyl, cyclodecyl and cyclododecyl, any of which groups may be substituted with substituents such as halogen, lower alkyl, alkoxy, and/or hydroxy groups.

The term "aryl" or "Ar" as employed herein by itself or as part of another group refers to monocyclic or bicyclic aromatic groups containing from 6 to 10 carbons in the ring portion, such as phenyl, or naphthyl. Aryl (or Ar), phenyl or naphthyl may include substituted aryl, substituted phenyl or substituted naphthyl, which may include 1, 2, 3, 4 or 5 substituents on either the Ar, phenyl or naphthyl such as lower alkyl, cyano, amino, alkylamino, dialkylamino, nitro, carboxy, carboalkoxy, trifluoromethyl, halogen (Cl, Br, I or F), lower alkoxy, arylalkoxy, hydroxy, alkylthio, alkylsulfinyl, alkylsulfonyl, arylthio, arylsulfinyl and/or arylsulfonyl.

Thus, a phenyl group $R^3$ may include 3, 4 or 5 substituents such as alkyl, for example, pentamethyl and 2,4,6-tri-isopropyl, and halo, for example, pentafluoro.

The term "aralkyl", "aryl-alkyl" or "aryl-lower alkyl" as used herein by itself or as part of another group refers to lower alkyl groups as discussed above having an aryl substituent, such as benzyl.

The term "lower alkoxy", "alkoxy" or "aralkoxy" includes any of the above lower alkyl, alkyl or aralkyl groups linked to an oxygen atom.

The term "halogen" or "halo" as used herein by itself or as part of another group refers to chlorine, bromine, fluorine or iodine with chlorine being preferred.

The term "lower alkenyl" or "alkenyl" as employed herein by itself or as part of another group includes a carbon chain of up to 16 carbons, preferably 3 to 10 carbons, containing one double bond which will be separated from "N" by at least one saturated carbon moiety such as —(CH$_2$)$_{q'}$— where q' can be 1 to 14, such as 2-propenyl, 2-butenyl, 3-butenyl, 2-pentenyl, 4-pentenyl and the like, and may include a halogen substituent such as I, Cl, or F.

The term "lower alkynyl" or "alkynyl" as employed herein by itself or as part of another group includes a carbon chain of up to 16 carbons, preferably 3 to 10 carbons, containing one triple bond which will be separated from "N" by at least one saturated carbon moiety such as —(CH$_2$)$_{q'}$— where q' can be 1 to 14, such as 2-propynyl, 2-butynyl, 3butynyl and the like.

The term "heteroaryl" or heteroaromatic by itself or as part of another group refers to a 5- to 10-membered aromatic ring(s) which includes 1, 2, 3 or 4 hetero atoms such as nitrogen, oxygen or sulfur, such as

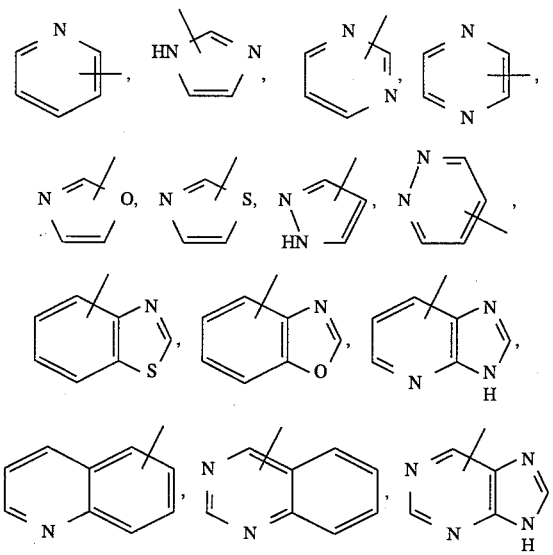

and the like. The heteroaryl rings may optionally be fused to aryl rings defined previously. The heteroaryl rings may optionally include 1 or 2 substituents such as halogen (Cl, Br, F or CF$_3$), lower alkyl, lower alkoxy, carboxy, amino, lower alkylamino and/or dilower alkylamino.

The term "cycloheteroalkyl" as used herein refers to a 5-, 6- or 7-membered saturated ring which includes 1 or 2 hetero atoms such as nitrogen, oxygen and/or sulfur, such as

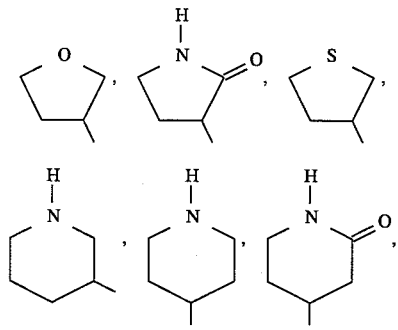

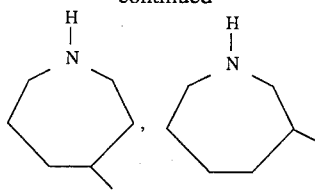

and the like.

The term "azacycloalkenyl" as used herein refers to a 4- to 8-membered ring such as

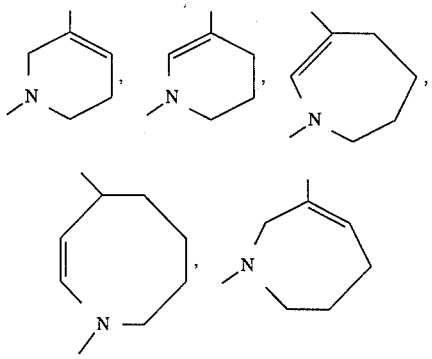

The term "amino acid side chain" refers to any of the known alpha-amino acids such as arginine, histidine, alanine, glycine, lysine, glutamine, leucine, valine, serine, homoserine, allothreonine, naphthylalanine, isoleucine, phenylalanine and the like.

The thrombin inhibitor compounds of formulae IV and IVA can be obtained as pharmaceutically acceptable acid addition salts by reacting the free base with an acid, such as hydrochloric, hydrobromic, fumaric, hydroiodic, nitric, sulfuric, phosphoric, acetic, citric, maleic, succinic, lactic, tartaric, gluconic, benzoic, methanesulfonic, ethanesulfonic, 2-hydroxyethanesulfonic, 1,2-ethanedisulfonic, benzenesulfonic, p-toluenesulfonic acid or the like.

The compounds of formulae IV and IVA are serine protease inhibitors, and in particular may inhibit thrombin, Factor Xa, and/or trypsin. The compounds of the present invention are useful for the treatment or prophylaxis of those processes which involve the production and/or action of thrombin. This includes a number of thrombotic and prothrombotic states in which the coagulation cascade is activated which include, but are not limited to, deep vein thrombosis (DVT), disseminated intravascular coagulopathy (DIC), Kasabach-Merritt syndrome, pulmonary embolism, myocardial infarction, stroke, thromboembolic complications of surgery (such as hip replacement and endarterectomy) and peripheral arterial occlusion. In addition to its effects on the coagulation process, thrombin has been shown to activate a large number of cells (such as neutrophils, fibroblasts, endothelial cells, smooth muscle cells). Therefore, the above compounds may also be useful for the treatment or prophylaxis of adult respiratory distress syndrome, septic shock, septicemia, inflammatory responses which include, but are not limited to, edema, acute or chronic atherosclerosis, and reperfusion damage.

The above compounds may also be useful in treating neoplasia/metastasis (in particular those which utilize fibrin)

and neurodegenerative diseases such as Alzheimer's disease and Parkinson's disease. In addition, the above compounds may be useful to prevent restenosis following arterial injury induced by endogenous (rupture of an atherosclerotic plaque) or exogenous (invasive cardiological procedure) events.

The above compounds may also be used as an anticoagulant in extracorpeal blood circuits, such as those necessary in dialysis and surgery (such as coronary artery bypass surgery).

The above compounds may also be used in combination with thrombolytic agents, such as tissue plasminogen activator (natural or recombinant), streptokinse, urokinase, prourokinase, anisolated streptokinase plasminogen activator complex (ASPAC), animal salivary gland plasminogen activators, and the like. The above compounds may act in a synergistic fashion to prevent reocclusion following a successful thrombolytic therapy and/or reduce the time to reperfusion. The above compounds may also allow for reduced doses of the thrombolytic agent to be used and therefore minimize potential hemorrhagic side-effects.

The above compounds may also be used in combination with other antithrombotic or anticoagulant drugs such as thromboxane receptor antagonists, prostacyclin mimetics, phosphodiesterase inhibitors, fibrinogen antagonists, and the like.

The above compounds that inhibit trypsin may also be useful for the treatment of pancreatitis.

The above compounds of formula IV or IVA can be administered orally or parenterally to various mammalian species known to be subject to such maladies, e.g., humans, cats, dogs and the like in an effective amount within the dosage range of about 0.1 to about 100 mg/kg, preferably about 0.2 to about 50 mg/kg and more preferably about 0.5 to about 25 mg/kg (or from about 1 to about 2500 mg, preferably from about 5 to about 2000 mg) on a regimen in single or 2 to 4 divided daily doses.

The active substance can be utilized in a composition such as tablet, capsule, solution or suspension containing about 5 to about 500 mg per unit of dosage of active compound IV. They may be compounded in conventional matter with a physiologically acceptable vehicle or carrier, excipient, binder, preservative, stabilizer, flavor, etc., as called for by accepted pharmaceutical practice.

It will be appreciated that guanidine moiety

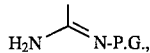

is used interchangeably with its tautomer

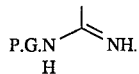

The following Examples represent preferred embodiments of the first embodiment of the present invention. Unless otherwise indicated, all temperatures are expressed in degrees Centigrade.

EXAMPLE 1

[[4-(Aminomethyl)-1-piperidinyl]iminomethyl]carbamic acid, phenylmethyl ester

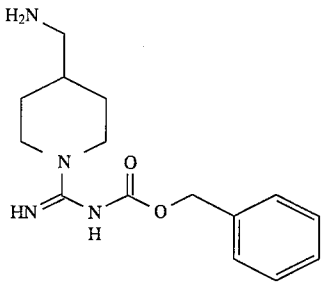

A.

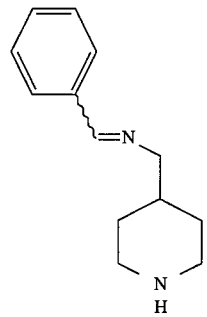

A 500 mL, round-bottomed flask equipped with Dean-Stark trap was sequentially charged with 4-aminomethylpiperidine (14.84 g, 129.96 mmole), toluene (250 mL), and benzaldehyde (14.98 g, 141.16 mmole). The mixture was heated to reflux under an argon atmosphere and stirred overnight (18 h). The reaction was cooled to room temperature and the toluene was removed in vacuo. Residual toluene was removed under high vaccuum to provide 28.14 g of the title compound as an orange oil (quantitative yield). The crude product was carried directly into the next step.

B.

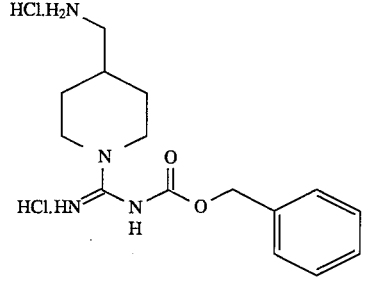

A 500 mL, round-bottomed flask was sequentially charged with Part A Schiff base (21.20 g, 104.8 mmole), acetonitrile (200 mL), [imino(1H-pyrazol-1-yl)methyl]carbamic acid, phenylmethyl ester (31.50 g, 128.96 mmole) and 1,8-diazabicyclo[5.4.0]-undec-7-ene (DBU) (18 mL, 120.36 mmole). After stirring for five minutes, the solution became clear yellow. The reaction was heated to 50° C. and stirred under a nitrogen atmosphere for 16 h. After the reaction had cooled to room temperature, 12N hydrochloric acid (36 mL, 432 mmole, reaction mixture reached pH 1) was added over 20 minutes. The reaction was stirred for 2.5 h at room temperature. The mixture was concentrated in vacuo to a yellow oil and isopropanol (35 mL) was added. With stirring, acetonitrile (250 mL) was added resulting in the separation of an oil. The mixture was heated to 40° C. providing a clear solution which was seeded. Within five minutes a white solid crystallized from solution. The slurry was stirred for an additional 40 minutes at 40° C. and then cooled to room temperature and stirred overnight. The product was collected by filtration and washed with 1:1 ethyl acetate/hexane (1×100 mL), 1:3 ethyl acetate/hexane (1×100 mL), and hexane (3×100 mL). Residual solvents were removed under high vaccuum to provide 29.95 g of an 11:1 mixture of title compound:4-aminomethyl piperidine, dihydrochloride salt as a white solid (79%).

C.
[[4-(Aminomethyl)-1-piperidinyl]-iminomethyl]carbamic acid, phenylmethyl ester Sodium hydroxide (4.45 g, 111.25 mmole) was dissolved in 150 mL of deionized water. A mixture of Part B compound and the 4-aminomethyl piperidine, dihydrochloride salt (prepared in Part B, 16.18 g, 44.54 mmole) was added (pH of the cloudy solution was 13) and the mixture was extracted with dichloromethane (1×200 mL and 2×100 mL). The organic layers were combined and washed with brine (1×200 mL), dried (MgSO₄), filtered and concentrated in vacuo to provide the title compound as a white foam (12.29 g, 95%).

EXAMPLE 2

N-[[(1-Aminoiminomethyl)-4-piperidinyl]methyl]-1-[N-(methylsulfonyl)-D-phenylalanyl]-L-prolinamide, acetate (1:1)

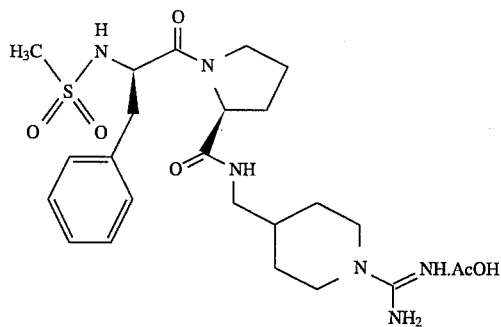

A. [N-(Methylsulfonyl)-D-phenylalanyl]-L-proline

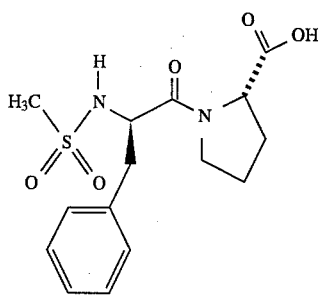

A(1).

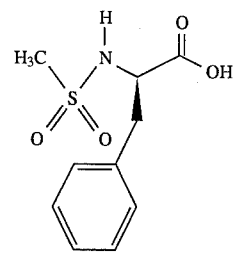

D-Phenylalanine (15.01 g, 90.865 mmol) was weighed into a 250-mL, 5-necked, round-bottomed flask equipped with thermocouple, pH probe, overhead stirrer and two addition funnels (one a constant-rate funnel to ensure even addition of methanesulfonyl chloride). Sodium hydroxide (3.642 g, 91.05 mmol) was dissolved in 90 mL of deionized water and added to the reaction flask. With stirring, the mixture became a clear solution. The internal temperature was brought to −2° C. (pH 12.3). With rapid stirring, methanesulfonyl chloride (5.0 mL, 64.60 mmol) was added via the constant-rate addition funnel. Once pH 11 was reached, 6N NaOH was added dropwise to maintain the pH at 10.9±0.2. A second portion of methanesulfonyl chloride (4.2 mL, 54.26 mmol) was then added while maintaining the pH at 10.5±0.2 (internal temperature <8°) by dropwise addition of 6 N sodium hydroxide. Once the pH had stabilized at 10.5, HPLC anlysis of an aliquot showed a 9:1 mixture of the title compound to D-phenylalanine. A third portion of methanesulfonyl chloride (1.2 mL, 15.5 mmol) was then added at 0° over 5 minutes while maintaining the pH at 10.5±0.2. After the addition was complete and the pH had stabilized at 10.4, the reaction mixture was brough to pH 13 with 6N sodium hydroxide, allowed to warm to 15° C. over 2 hr, and then washed with methyl isobutylketone (2×100 mL). The aqueous layer was acidified to pH 1 with 6N hydrochloric acid and extracted with ethyl acetate (1×200 mL and 2×150 mL). The ethyl acetate layers were combined and washed with brine (1×150 mL), dried over MgSO₄, and concentrated in vacuo to yield a yellow oil (18.36 g, 83%). HPLC analysis of the oil showed a 7:1 mixture of the title compound to [N-methylsulfonyl-D-phenylalanine]-D-Phenylalanine. This material was carried into the next step without further purification.

A(2).

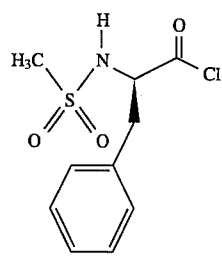

The Part A(1) mixture of N-methylsulfonyl-D-phenylalanine and [N-methylsulfonyl-D-phenylalanine]-D-phenylalanine (18.36 g, 75.47 mmol) was dissolved in 250 mL of dichloromethane under an argon atmosphere. Heating to reflux and stirring for about 15 minutes was necessary to completely dissolve the material. After the solution had cooled to room temperature, DMF (0.23 mL, 2.97 mmol) was added and the internal temperature was further lowered to 3° C. (ice bath). Oxalyl chloride (7.4 mL, 84.85 mmol) was added in a steady stream over 2 minutes. After the addition was complete, the reaction was allowed to warm to room temperature over 3 hours and then stirred at room temperature for one hour. The mixture was concentrated in vacuo to a yellow oil, toluene (100 mL) was added and the solution was concentrated to a yellow oily solid (19.89 g, 101%). This material was stored in a refrigerator overnight under an argon atmosphere and was carried into the next step without further purification.

A(3).
[N-(Methylsulfonyl)-D-phenylalanyl]-L-proline

The crude Part A(2) acid chloride prepared above was dissolved in 120 mL of toluene, with heating to 40° C., and then cooled to room temperature under an argon atmosphere. L-proline (13.11 g, 113.87 mmol) was weighed into a 500 mL, 5-necked flask equipped with two addition funnels, thermocouple, pH probe and overhead stirrer. Sodium hydroxide (2.68 g, 67 mmol) was dissolved in 120 mL of deionized water and added to the reaction flask. The proline readily dissolved with stirring to give a clear solution which was cooled to 0° C. The initial pH was 12.15. The acid chloride-toluene solution was added dropwise to the rapidly stirring proline solution until the pH reached 11.0 (internal temperature maintained at <5° C.). The remainder of the acid chloride was added dropwise over 25 minutes while maintaining the internal temperature below 5° C. and the pH at 11.0±0.2 by dropwise addition of 4N sodium hydroxide (23 mL total). The acid chloride was washed in with 20 mL of toluene. After the addition was complete and the pH had stabilized to 11.1, the icebath was removed and the reaction was allowed to warm to 12° C. over 30 minutes. The aqueous and organic layers were separated and the basic aqueous layer was washed with ethyl acetate (1×100 mL, discard). Ethyl acetate (350 mL) was added to the basic aqueous solution and while stirring vigorously, the mixture was acidified with 6N hydrochloric acid to pH 1. The organic and aqueous layers were separated and the acidic aqueous was extracted with ethyl acetate (2×150 mL). The combined ethyl acetate layers from the acidic extractions were washed with brine (1×150 mL), dried (MgSO$_4$), filtered, and concentrated in vacuo to a total weight of 260 g, providing a slurry of the title compound in the ethyl acetate. With stirring, 260 mL of hexane was added and the slurry was stirred for 4 h at room temperature. The white crystalline solid was collected by filtration, washed with hexane/ethyl acetate (2:1, 2×100 mL) followed by hexane (2×100 mL). Drying in vacuo provided the title compound (20.84 g, 84%) as a white crystalline solid.

B(1).

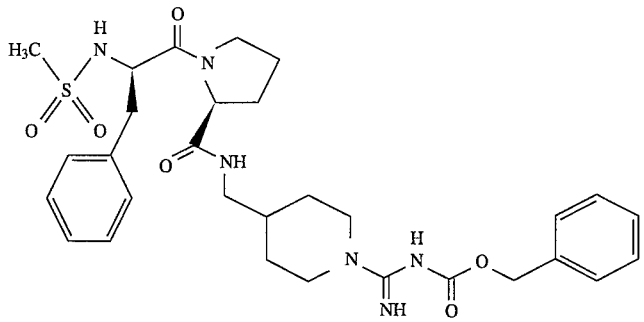

A 500 mL, round-bottomed flask was sequentially charged with Example 1 compound (10.41 g, 35.84 mmole), isopropanol (60 mL), deionized water (60 mL), and Part A compound (10.00 g, 29.38 mmole). Under an argon atmosphere, the clear yellow solution was brought to 10° C. and 1-hydroxybenzotriazole hydrate (4.40 g, 32.56 mmole) was added. The mixture was further cooled to 4° C. and 1-(3-dimethylamino-propyl)-3-ethlycarbodiimide hydrochloride (6.53 g, 34.06 mmole) was added. The resulting clear solution was stirred between 1 and 4° C. for 3 hours and then slowly warmed to 20° C. over 14 hours. A portion of the solvent (62 g) was removed in vacuo. Ethyl acetate (250 mL) was added. With stirring, deionized water (465 mL) and 6N hydrochloric acid (40 mL) were added. The aqueous and organic layers were separated and the aqueous layer was washed with ethyl acetate (1×100 mL). The combined ethyl acetate layers were concentrated to 100 g and extracted with 0.5N hydrochloric acid (2×60 mL). The combined acidic aqueous layers were brought to pH 6 with 12N sodium hydroxide and extracted with dichloromethane (1×250 mL and 2×150 mL). The dichloromethane layers were combined and washed with deionized water (1×150 mL) and brine (1×150 mL), dried (MgSO$_4$), filtered and concentrated in vacuo. The residual solvents were 10 removed under high vacuum to provide title CBZ-protected compound as a white foam (15.44 g, 83% yield, corrected for ethyl acetate in $^1$H NMR). The crude product was carried directly into the next step.

B(2).
N-[[1-(Aminoiminomethyl)-4-piperidinyl]-methyl]-1-[N-(methylsulfonyl)-D-phenylalanyl]-L-prolinamide, acetate (1:1)

A solution of Part B(1) CBZ-protected compound (13.22 g, 21.58 mmole) in MeOH (150 mL) was purged with argon for ten minutes. Palladium hydroxide on carbon (1.32 g) was added and the mixture was again purged with argon for ten minutes. The solution was then purged with hydrogen and the reaction was stirred under a hydrogen atmosphere for 2.5 hours. After the reaction was complete by HPLC, the mixture was purged with argon, filtered through celite and the celite washed with methanol (2×100 mL). Acetic acid was added and the solution was concentrated in vacuo to an oil. Isopropanol (100 mL) was added and the solution concentrated in vacuo to 45 g. The thick solution was seeded. With stirring, 180 mL of acetonitrile was added over 20 minutes. Within three hours, a white solid crystallized from solution and the resulting slurry was allowed to stir overnight at room temperature. The solid was collected by filtration and washed with acetonitrile (1×50 mL), 1:1 hexane/ethyl acetate (1×60 mL), and hexane (2×50mL). The product was dried in vacuo to yield the title compound as a white crystalline solid (8.83 g, 76%).

Following the procedure of Example 1 Part A, except substituting for 4-aminomethylpiperidine, the compound set out below in Table A, the corresponding protected compound III is formed which is reacted with protected guanylpyrazole II to form intermediate I following the procedure as described in Example 1.

TABLE A

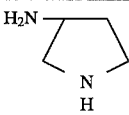

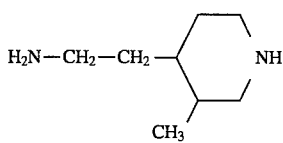

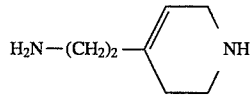

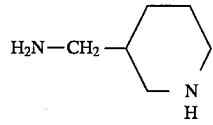

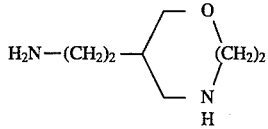

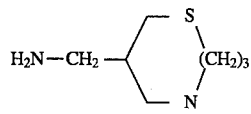

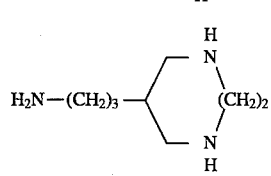

Following the procedure of Example 2, except employing the intermediate formed from Table A amine, the corresponding thrombin inhibitor IV is formed.

What is claimed is:

1. A process for preparing a guanidine intermediate of the structure

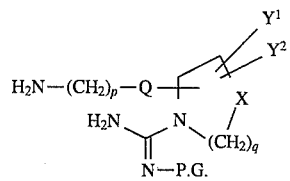

wherein p is 0, 1 or 2;
Q is a single bond or

$Y^1$ and $Y^2$ are independently H, lower alkyl or halo;
X is $CH_2$, —CH=CH—, O, S or NH;
q is 0, 1, 2, 3 or 4 if X is $CH_2$ or —CH=CH—;
q is 2, 3 or 4 if X is O, S or NH;
and P.G. is an amine protecting group, which comprises providing a protected guanylpyrazole of the structure

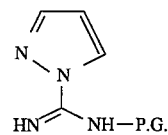

where P.G. is as defined above, and reacting the protected guanylpyrazole with a heterocyclic compound of the structure

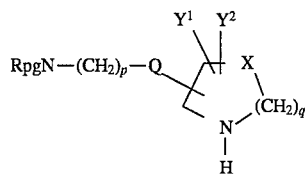

where p, Q, X, q and $Y^1$ and $Y^2$ are as defined above and Rpg is an N-protecting group, in the presence of a basic catalyst, to form the guanidine intermediate.

2. The process as defined in claim 1 wherein the basic catalyst is 1,8-diazabicyclo[5.4.0]undec-7-ene.

3. The process as defined in claim 1 wherein the protected guanylpyrazole is employed in a molar ratio to the heterocyclic compound within the range from about 1:1 to about 3:1.

4. The process as defined in claim 1 wherein the reaction is carried out at a temperature within the range from about 20° C. to about 70° C.

5. The process as defined in claim 1 wherein the Rpg N-protecting group is =$CHC_6H_5$, benzyloxycarbonyl (CBZ) or t-butoxycarbonyl (BOC).

6. The process as defined in claim 1 wherein Q is a single bond, $Y^1$ and $Y^2$ are each H, X is $CH_2$, q is 1 or 2.

7. The process as defined in claim 1 wherein the guanidine intermediate prepared is 5,610,308

[Structure: 4-(aminomethyl)piperidine with N-C(=NH)NH-P.G. substituent on ring N, showing NH₂-(CH₂)ₚ- group]

8. The process as defined in claim 7 wherein the heterocyclic compound is

[Structure: 4-((benzylideneamino)methyl)piperidine, N=CHC₆H₅ on CH₂ attached to piperidine with NH]

9. A process for preparing a heterocyclic compound of the structure

[Structure: RpgN—(CH₂)ₚ—Q—[ring with Y¹, Y², X, (CH₂)q, NH]]

wherein p is 0, 1 or 2;

Q is a single bond or $$\begin{array}{c} | \\ C=O \\ | \end{array}$$
;

$y^1$ and $y^2$ are independently H, lower alkyl or halo;

X is $CH_2$, —CH=CH—, O, S or NH;

q is 0, 1, 2, 3 or 4 if X is $CH_2$ or —CH=CH—;

q is 2, 3 or 4 if X is O, S or NH;

and Rpg is an N- protecting group, which comprises providing an unprotected amino compound of the structure

[Structure: H₂N—(CH₂)ₚ—Q—[ring with Y₁, Y², X, (CH₂)q, NH]]

wherein p, Q, Y¹, Y², X and q are as defined above, and reacting the unprotected amino compound with an aldehyde at a temperature within the range from about 20° C. to about 120° C., to form the heterocyclic compound.

10. The process as defined in claim 9 wherein the aldehyde is benzaldehyde.

11. A process for preparing a sulfonamido heterocyclic thrombin inhibitor of the structure

[Structure of sulfonamido thrombin inhibitor: R³—S(=O)₂—N(H)—C(H)(R)—C(=O)—N(H)—CH(R¹)(CH(R²)...)—(CH₂)ₙ—C(=O)—NH—(CH₂)ₚ—Q—[ring with Y¹, Y², X, (CH₂)q, N—C(=NH)NH₂]]

wherein R is hydrogen, hydroxyalkyl, aminoalkyl, amidoalkyl, alkyl, cycloalkyl, aryl, arylalkyl, alkenyl, alkynyl, arylalkoxyalkyl, or an amino acid side chain, either protected or unprotected;

$R^1$ and $R^2$ are independently hydrogen, lower alkyl, cycloalkyl, aryl, hydroxy, alkoxy, oxo (also referred to as keto), thioxo, thioketal, thioalkyl, thioaryl, amino or alkylamino; or $R^1$ and $R^2$ together with the carbons to which they are attached form a cycloalkyl, aryl, or heteroaryl ring; and $R^3$ is lower alkyl, aryl, arylalkyl, heteroaryl, quinolinyl or tetrahydroquinolinyl;

n is 0, 1 or 2;

$y^1$ and $y^2$ are independently H, lower alkyl or halo;

p is 0, 1 or 2;

Q is a single bond or $$\begin{array}{c} | \\ C=O \\ | \end{array}$$;

X is $CH_2$,—CH=CH—, O, S or NH;

q is 0, 1, 2, 3 or 4 if X is $CH_2$, or —CH=CH—;

q is 2, 3 or 4 if X is O, S or NH;

provided that where X is a hetero atom, then there must be at least a 2-carbon chain between X and any N atom in the ring or outside the ring;

which process comprises providing a protected guanylpyrazole of the structure

[Structure: pyrazole with C(=NH)NH—P.G. substituent]

where P.G. is an amine protecting group, reacting the protected guanylpyrazole with a heterocyclic compound of the structure

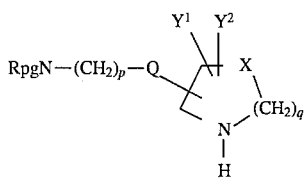

where p, Q, X, q and $Y^1$ and $Y^2$ are as defined above and Rpg is an N-protecting group, in the presence of a basic catalyst, to form a guanidine intermediate of the structure

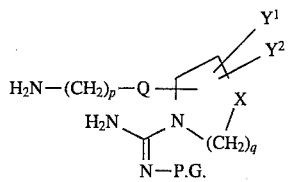

wherein p is 0, 1 or 2;

Q is a single bond or

reacting the guanidine intermediate with an amino acid of the structure

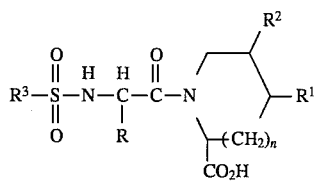

in a carbodiimide coupling reaction in the presence of a coupling agent and a base to form the protected amide compound

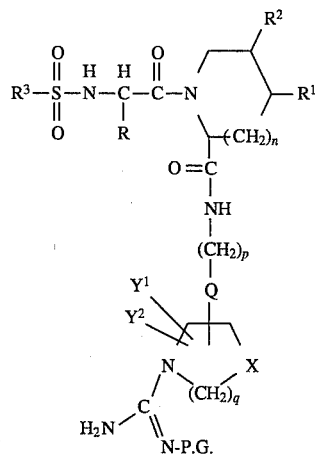

treating the protected amide compound with a deprotection agent to form the guanidine thrombin inhibitor.

12. The process as defined in claim 10 wherein the coupling reaction is carried out in the presence of ethyl 3-(3-dimethylamino)propyl carbodiimide hydrochloride, dicyclohexylcarbodiimide or diisopropylcarbodiimide; and 1-hydroxybenzotrizaole monohydrate, and optionally in the presence of a base which is N-methyl morpholine or triethylamine.

13. The process as defined in claim 10 wherein the starting acid compound has the structure

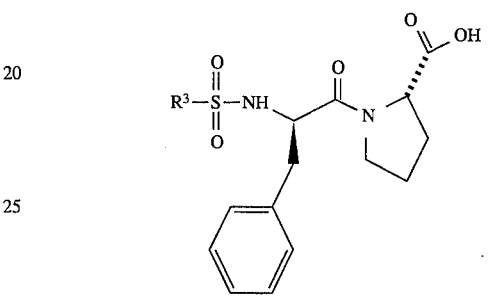

wherein $R^3$ is alkyl, aryl, or arylalkyl.

14. The process as defined in claim 13 wherein the guanidine thrombin inhibitor as formed has the structure

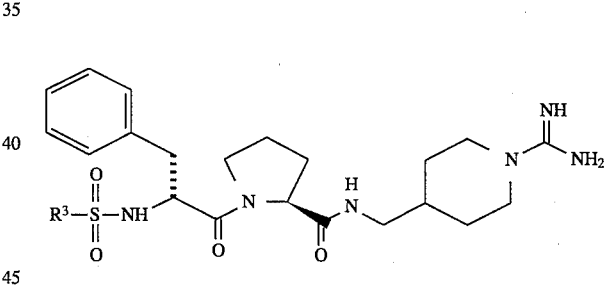

where $R^3$ is preferably CH3 or benzyl.

15. The process as defined in claim 10 wherein the guanidine intermediate is employed in a molar ratio to the acid compound whithin the range from about 1:1 to about 3:1.

16. The process as defined in claim 10 wherein the coupling reaction will be carried out at a temperature within the range from about 0° C. to about 30° C.

* * * * *